US009395360B2

(12) United States Patent
Trau et al.

(10) Patent No.: US 9,395,360 B2
(45) Date of Patent: Jul. 19, 2016

(54) MICROARRAY SYSTEM AND A PROCESS FOR PRODUCING MICROARRAYS

(71) Applicant: National University of Singapore, Singapore (SG)

(72) Inventors: Dieter Trau, Singapore (SG); Wen-Tso Liu, Singapore (SG); Kian Kok Johnson Ng, Singapore (SG)

(73) Assignee: NATIONAL UNIVERSITY OF SINGAPORE, Singapore (SG)

( * ) Notice: Subject to any disclaimer, the term of this patent is extended or adjusted under 35 U.S.C. 154(b) by 452 days.

(21) Appl. No.: 14/059,164

(22) Filed: Oct. 21, 2013

(65) Prior Publication Data
US 2014/0045721 A1  Feb. 13, 2014

Related U.S. Application Data

(62) Division of application No. 12/376,040, filed as application No. PCT/SG2007/000232 on Aug. 3, 2007, now Pat. No. 8,927,465.

(60) Provisional application No. 60/835,648, filed on Aug. 3, 2006.

(51) Int. Cl.
*G01N 33/543* (2006.01)
*C40B 60/02* (2006.01)
(Continued)

(52) U.S. Cl.
CPC ....... *G01N 33/54313* (2013.01); *B01J 19/0046* (2013.01); *C12Q 1/6834* (2013.01);
(Continued)

(58) Field of Classification Search
CPC ........ C40B 50/16; C40B 50/18; C40B 60/14; G06T 5/50; G06T 7/0008; G06T 7/0024; G06T 7/0081
See application file for complete search history.

(56) References Cited

U.S. PATENT DOCUMENTS 5,244,636 A  9/1993 Walt et al.
5,250,264 A  10/1993 Walt et al.
(Continued)

FOREIGN PATENT DOCUMENTS

WO    WO 9210092 A1    6/1992
WO    WO 9853093 A1    11/1998
(Continued)

OTHER PUBLICATIONS

Nolan J.P., et al. "Suspension Array Technology: Evolution of the flat-array paradigm", Trends in Biotechnology, vol. 20, pp. 9-12, Jan. 2002.
(Continued)

*Primary Examiner* — Jeremy C Flinders
(74) *Attorney, Agent, or Firm* — Leydig, Voit & Mayer, Ltd.

(57) ABSTRACT

A process for making a micro-array. The process comprises the step of depositing a population of microbeads on a substrate having at least one fiducial. The population being comprised of at least two sub-populations, preferably multiple sub-populations, each comprising a known active agent capable of specific binding with at least one target analyte. The said subpopulations are deposited sequentially and at discrete periods of each other. The process also comprises the step of making images of the substrate after deposition of each subpopulation. The images are then compared using the fiducial as a reference to thereby determine the location of each microbead and to identify the subpopulation, and its known active agent, based on differences between each image. Also disclosed in a system for using the microarray.

12 Claims, 4 Drawing Sheets

(51) Int. Cl.

| | |
|---|---|
| *G06T 7/00* | (2006.01) |
| *G06T 5/50* | (2006.01) |
| *B01J 19/00* | (2006.01) |
| *C40B 30/04* | (2006.01) |
| *C40B 40/04* | (2006.01) |
| *G01N 21/64* | (2006.01) |
| *C40B 20/02* | (2006.01) |
| *C12Q 1/68* | (2006.01) |
| *C40B 50/16* | (2006.01) |
| *C40B 60/14* | (2006.01) |
| *C40B 50/18* | (2006.01) |

(52) U.S. Cl.
CPC .............. *C12Q1/6883* (2013.01); *C40B 20/02* (2013.01); *C40B 30/04* (2013.01); *C40B 40/04* (2013.01); *G01N 21/6452* (2013.01); *G06T 5/50* (2013.01); *G06T 7/0008* (2013.01); *G06T 7/0028* (2013.01); *B01J 2219/0054* (2013.01); *B01J 2219/0074* (2013.01); *B01J 2219/00317* (2013.01); *B01J 2219/00459* (2013.01); *B01J 2219/00466* (2013.01); *B01J 2219/00648* (2013.01); *B01J 2219/00659* (2013.01); *B01J 2219/00677* (2013.01); *B01J 2219/00702* (2013.01); *B01J 2219/00722* (2013.01); *C40B 50/16* (2013.01); *C40B 50/18* (2013.01); *C40B 60/14* (2013.01)

(56) References Cited

U.S. PATENT DOCUMENTS

| | | | |
|---|---|---|---|
| 5,405,783 | A | 4/1995 | Pirrung et al. |
| 5,770,722 | A | 6/1998 | Lockhart et al. |
| 7,041,510 | B2 | 5/2006 | Seul et al. |
| 7,057,704 | B2 | 6/2006 | Seul et al. |
| 7,358,097 | B2 | 4/2008 | Seul et al. |
| 7,390,676 | B2 | 6/2008 | Seul et al. |
| 2002/0150909 | A1 | 10/2002 | Stuelpnagel et al. |
| 2004/0106114 | A1 | 6/2004 | Kocher |
| 2004/0185483 | A1 | 9/2004 | Stuelpnagel et al. |
| 2006/0041384 | A1 | 2/2006 | Kermani et al. |

FOREIGN PATENT DOCUMENTS

| | | |
|---|---|---|
| WO | WO 0016101 A2 | 3/2000 |
| WO | WO 00/47996 A2 | 8/2000 |
| WO | WO 0044939 A1 | 8/2000 |
| WO | WO 0047996 A2 | 8/2000 |
| WO | WO 0061281 A1 | 10/2000 |
| WO | WO 02/12897 A2 | 2/2002 |
| WO | WO 0212897 A2 | 2/2002 |
| WO | WO 2004066210 A1 | 8/2004 |

OTHER PUBLICATIONS

Li, A.X., et al.,"Multiplexed analysis of polymorphisms in the HLA gene complex using bead array chips" Tissue Antigens 63: pp. 518-528, Dec. 2004, Denmark.

Han, M., et al "Quantum-dot-tagged microbeads for multiplexed optical coding of biomolecules", Nature Biotechnology, vol. 19, pp. 631-635, Jul. 2001.

Tong, A.K., et al. "Combinatorial fluorescence energy transfer tags for multiplex biological arrays", Nature Biotechnology, vol. 19, pp. 756-759, Aug. 2001.

Lockhart, D.J., et al. "Multiplex Metallica", Nature Biotechnology, vol. 19, pp. 1122-1123, Dec. 2001.

Okamoto, T., et al. "Microarray fabrication with covalent attachment of DNA using Bubble Jet technology", Nature Biotechnology, vol. 18, pp. 438-441, Apr. 2000.

Cheung, Vivian G., et al. "Making and reading microarrays", Nature Genetics, vol. 21, pp. 15-19, Jan. 1999.

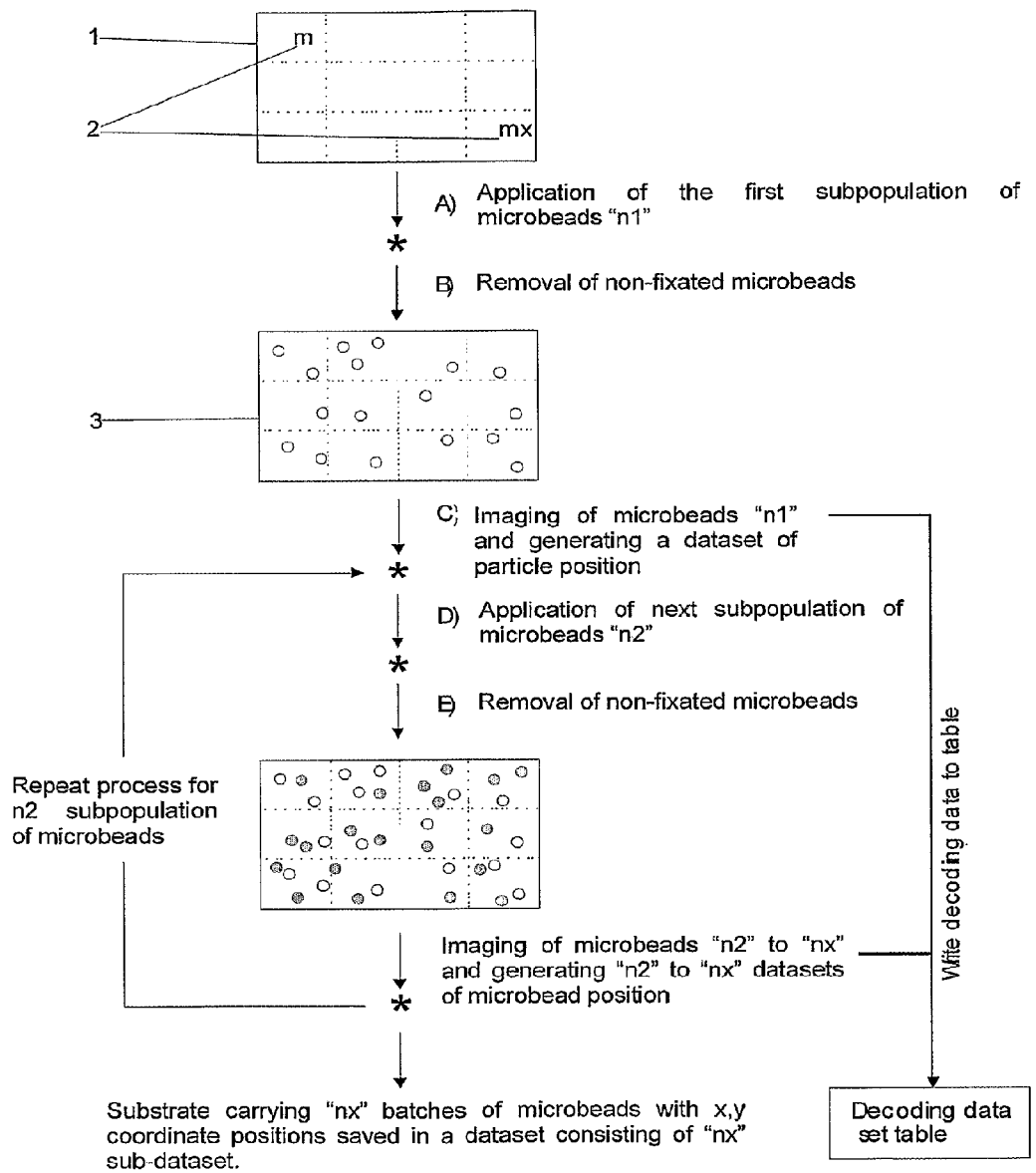

Figure 2

A) Providing the microbead based microarry and its unique encoding/decoding data table

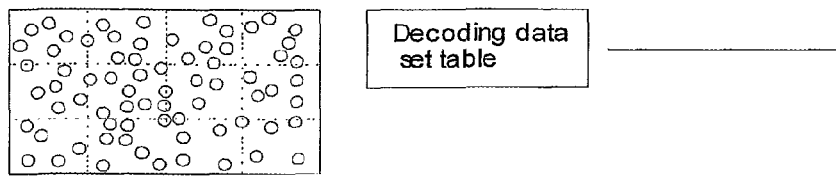

B) Incubating a sample with the microarray and performing bioassays based on i) hybridization or     ii) antibody antigen interaction elongation     iii) enzymatic reaction and causing optical signatures on the surface of the microbeads

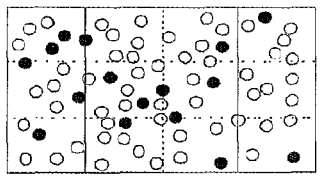

C) Reading out the microarray by imaging microbeads having an optical signature on their surface and determining the spatial position of each such microbead and creating a readout data table

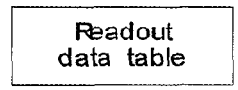

D) Combining and comparing the data of the encoding/decoding data table and the readout data table to identify microbeads in both data tables and therby decoding the microarray to identify the target analytes in the sample

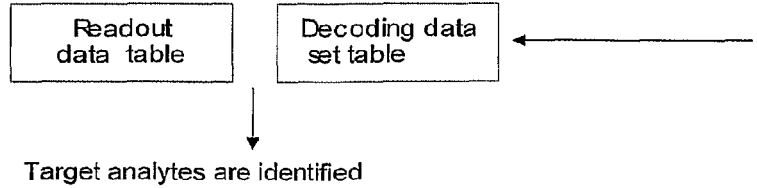

Target analytes are identified

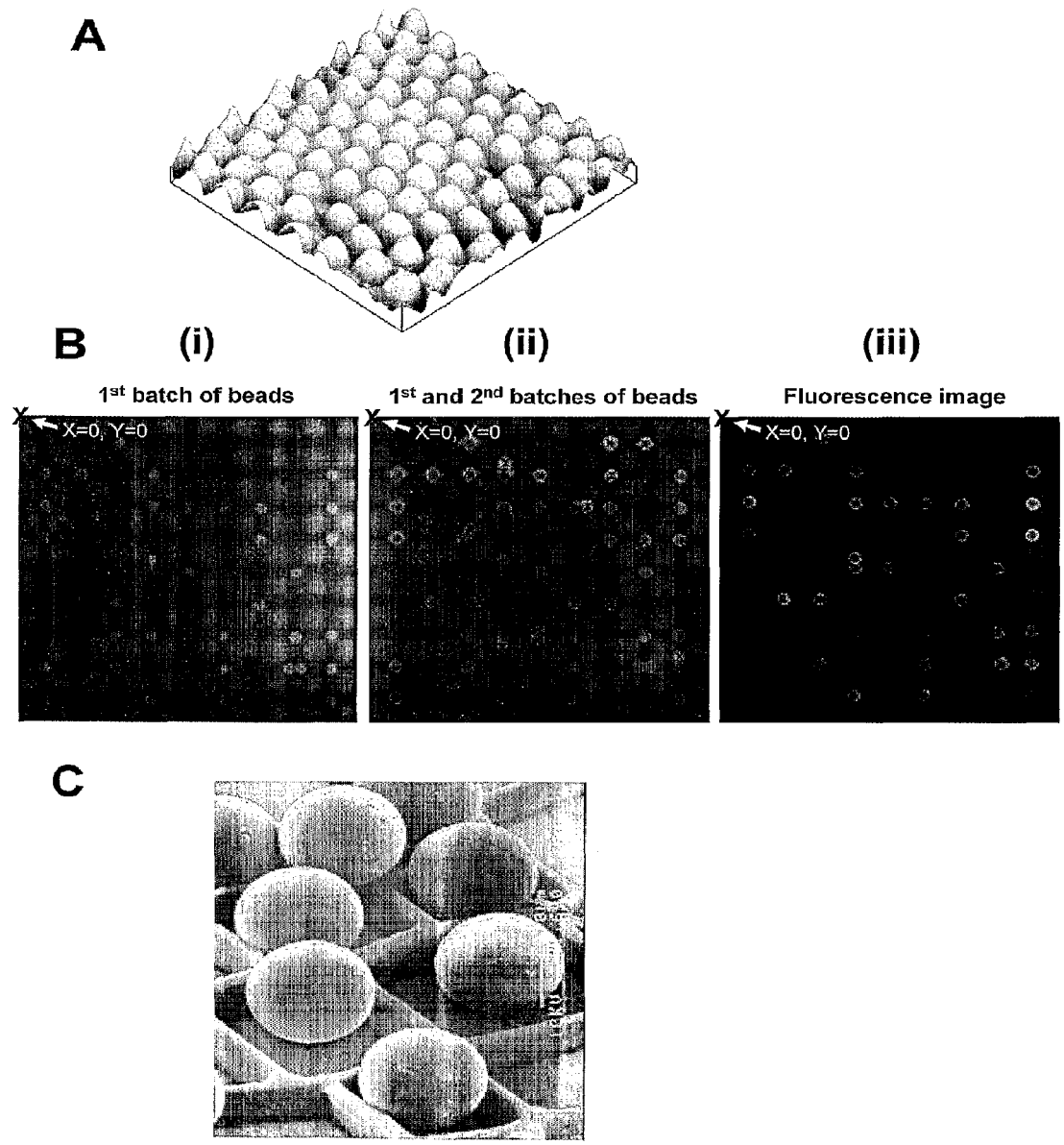

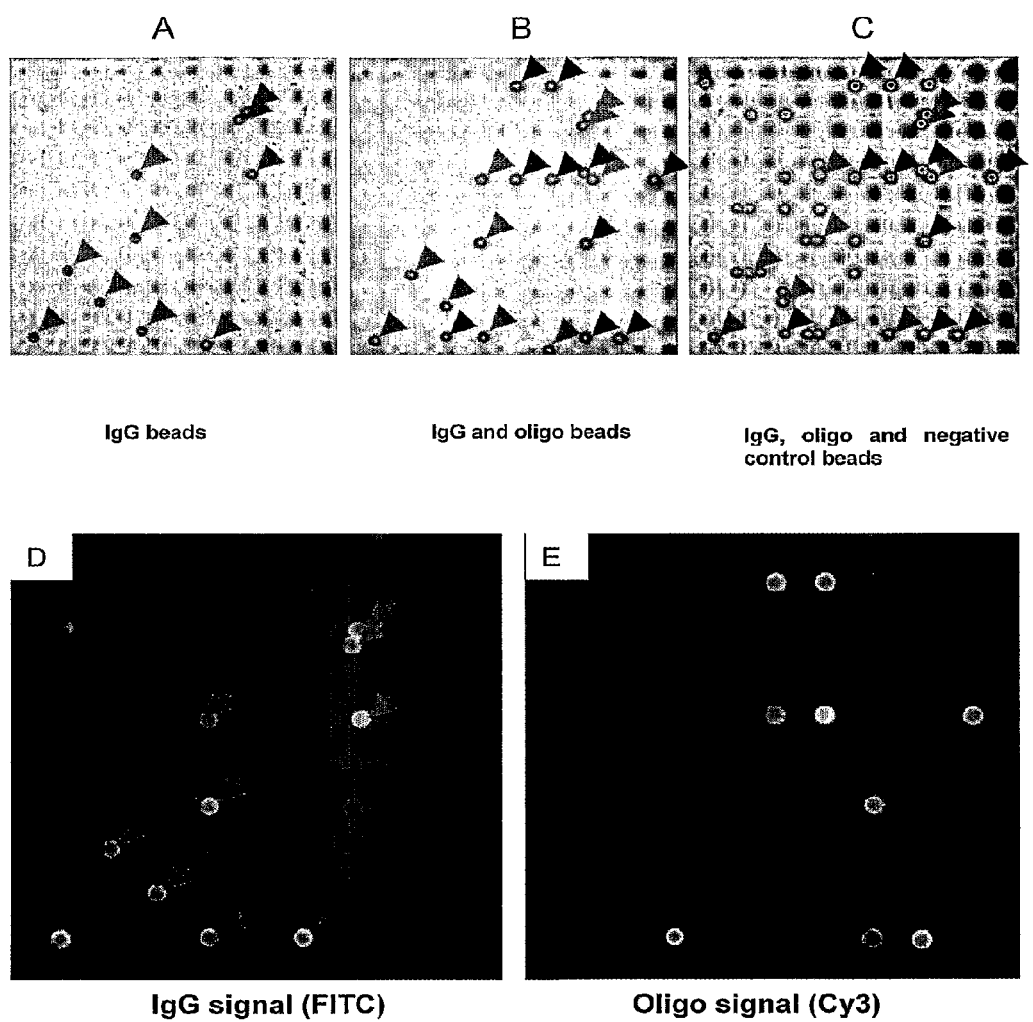

SEQUENCE LISTING

```
<160> NUMBER OF SEQ ID NOS: 2

<210> SEQ ID NO 1
<211> LENGTH: 18
<212> TYPE: DNA
<213> ORGANISM: Artificial sequence
<220> FEATURE:
<223> OTHER INFORMATION: oligonucleotide

<400> SEQUENCE: 1
gccctcacga tctcttcc                                                  18

<210> SEQ ID NO 2
<211> LENGTH: 20
<212> TYPE: DNA
<213> ORGANISM: Artificial sequence
<220> FEATURE:
<223> OTHER INFORMATION: oligonucleotide

<400> SEQUENCE: 2
aggaagagat cgtgagggca                                                20
```

MICROARRAY SYSTEM AND A PROCESS FOR PRODUCING MICROARRAYS

INCORPORATION OF PRIORITY APPLICATIONS

This application is a divisional of U.S. application Ser. No. 12/376,040 filed Oct. 13, 2009, which is a 371 national stage entry of International Application No. PCT/SG2007/000232 filed Aug. 3, 2007, which claims the benefit of U.S. Provisional Application No. 60/835,648 filed Aug. 3, 2006, each of which applications is herein incorporated by reference in its entirety.

INCORPORATION OF SEQUENCE LISTING

This application contains a sequence listing submitted electronically via EFS-web, which serves as both the paper copy and the computer readable form (CRF) and consists of a file entitled "085457-8001US01_seqlist.txt", which was created on Oct. 21, 2013, which is 4,096 bytes in size, and which is herein incorporated by reference in its entirety.

TECHNICAL FIELD

The present invention generally relates to microarrays for identifying the presence of target analytes in fluid samples. The present invention also relates to a process for making microarrays.

BACKGROUND

Microarrays are commonly fabricated by locating biomolecules onto flat substrates. Known technologies of microarray fabrication can be divided into two methods:
1) The position of the biomolecule is specified prior to its transfer on the substrate ("Ordered biomolecule deposition"); and
2) The position of the biomolecule is randomly allocated on the substrate ("Random biomolecule deposition").

Ordered biomolecule deposition is by far the most usual way for microarray production. A detailed experimental description is given in: Schena, M., "DNA Microarrays", Oxford University Press, 2001. A technology review is also given in: Vivian G., at al. "Making and reading microarrays", Nature Genetics 21, 15-19, 1999. In known microarray production methods, robots carry out the transfer of analyte-targeting biomolecules to substrates and ordered arrays are created. Usually biomolecules are dissolved in a buffer. Typical transfer volumes are between 0.1 nl and 1 ml. Examples of biomolecules are DNA, oligonucleotides and proteins.

Different technologies are available to spot the biomolecule solution onto the substrate. Spotting technologies can be divided in two groups:
1) Technologies that have no physical contact between the printer and the surface; and
2) Technologies that make use of physical contact between a printing tip and the substrate.

Technologies that belong to the first group are based on bubble-jet technologies in which a small droplet is produced and accelerated by means of piezoelectric induced or thermal induced pressure, or with the production of a droplet with a motor driven micro syringe (Okamoto T., et al. "Microarray fabrication with covalent attachment of DNA using Bubble Jet technology", Nature Biotechnology, 18, 438-441, 2000).

Technologies that belong to the second group use a printing tip that can hold a small volume of a sample solution and transfer a part of this solution to the substrate by making physical contact. The transferred volume depends on the print tip geometry, nature of the solvent and the hydrophobicity of the substrate.

In all of the abovementioned technologies, print heads or pins can be combined into groups (usually 8 to 64) to print multiple samples in parallel. The distance of spots printed in parallel is fixed due to the physical size of the printer heads or pins. This limits the minimal spot distance to 2 to 5 mm in a parallel printing step. To archive high spot density, multiple prints must be carried out with a small offset in the x and/or y direction.

In all of the above known methods, the number of spots printed is linear to the product of print heads and printing steps, thus limiting the production of high quantities of arrays.

The production time increases linearly with the number of chips produced and with the number of particular bio-recognition elements printed. The array density is limited due to the accuracy of the printing instrument. The disadvantage of robot-based techniques is the long time needed to produce a large number of arrays with high spot density.

Another microarray production technology is based on the synthesis of polymers directly onto the microarray substrate and is described in International PCT Patent Publication Number WO 9210092 and U.S. Pat. Nos. 5,405,783 and 5,770,722. These disclosed techniques are limited to oligonucleotides and utilize photolithography. The disclosed techniques are only economic if a very high number (thousands) of different oligonucleotide sequences are needed.

In random biomolecule deposition, biomolecule spots are created randomly onto a substrate. Common techniques use mixtures of microbeads or microbeads made from subpopulations. To determine which subpopulation a microbead belongs to, all of the microbeads must be encoded. Technologies to encode microbeads are based on their labeling with fluorophores of different color, labeling with micro microbeads carrying different colors (WO2004066210 HYBRID RANDOM BEAD/CHIP BASED MICROARRAY), by metal tags (Lockhart, D. J., at al. "Multiplex Metallica", Nature Biotechnology, 19, 1122-1123, 2001), by radio frequency tags, by fluorescence energy transfer tags (Tong, A. K., at al. "Combinatorial fluorescence energy transfer tags for multiplex biological assays", Nature Biotechnology, 19, 756-759, 2001), by oligonucleotide tags or with quantum-dots (Han, M., at al. "Quantum-dot-tagged microbeads for multiplexed optical coding of biomolecules", Nature Biotechnology 19, 631-635, 2001). Encoding by optical signatures (e.g. fluorescence) is further described in International PCT Patent Publication Numbers WO 0016101, WO 0061281, and WO 9853093. Methods that make use of fiber optic bundles with dyes attached to their distal ends instead of flat substrates are described in U.S. Pat. No. 5,244,636 and U.S. Pat. No. 5,250,264. The advantage of using optical fibers is to avoid the problem of interference of light which may arise from the use of different dyes.

Large numbers of polystyrene beads (~3.2 μm) can be assembled into a high density bead array chip in an etched silicon device by a method known as light-controlled electrokinetic assembly of microbeads near surfaces (LEAPS) (Li et al. Tissue Antigens 63: 518-528). In this method, the back side of a silicon wafer is placed in contact with a metal electrode. A counter electrode is then brought into contact with a suspended bead solution that is dispensed onto the wafer surface. Using an alternating current, beads can be moved to designated areas of low-impedance on the chip. An array of about 4000 beads has been successfully arrayed in a 300 µm×300 µm area, and applied in Single Nucleotide Polymorphism (SNP) analysis of the human leukocyte antigen gene complex. Although the analysis times are not reported, the ability to assemble thousands of individually addressable beads makes this bead array chip an attractive platform for high-throughput SNP genotyping.

In known methods, the information of individual spots or beads is deciphered after all of the beads have been randomly placed on the substrate, typically at the same time the array is used for analysis. The microbeads are decoded and the decode data is combined with data obtained from reading changes of microbead properties caused by the analyte. Automated information processing for decoding of encoded microbeads is described in International PCT Patent Publication Number WO 0047996.

A disadvantage of decoding procedures associated with such methods as those disclosed in WO 0047996 is that the decoding step can be complex and time consuming. In WO 0047996, the decoding step requires that a first plurality of decoding binding ligands are added to a random array of microbeads comprising immobilized binding ligands and a first data image is created. A fiducial is used to generate a first registered data image. A second plurality of decoding binding ligands are added to the random array of microbeads and a second data image is created. The fiducial is used to generate a second registered data image. A computer system is then used to compare the first and the second registered data images to identify the location of at least two bioactive agents. However, the use of decoding binding ligands taught in WO 0047996 has significant disadvantages. In particular, a long time is needed to read the encoded code of all microbeads, as discussed in: Nolan J. P. et al. "Suspension array technology: evolution of the flat-array paradigm", Trends in Biotechnology, 20, 9-12, 2002.

Furthermore the creation of an encoding system is difficult and requires multiple processing steps. Read out instruments are required to decode encoded microbeads. For example, microbead code created by different fluorophores require multiple wavelength measurements, thereby requiring multiple light sources and filters. These instruments are sophisticated and expensive. All of the above factors make manufacturing the microarrays more complex, time consuming and thereby more expensive to implement.

There is a need to provide a process for making microarrays that overcomes, or at least ameliorates, one or more of the disadvantages described above.

There is a need to provide a system for identifying the presence of a target analyte that overcomes, or at least ameliorates, one or more of the disadvantages described above.

There is a need to provide a process for making microarrays that avoids the need to decode the microarrays after manufacture.

SUMMARY

According to a first aspect, there is provided a process for making a micro-array comprising the steps of:

depositing a population of microbeads on a substrate having at least one fiducial, said population being comprised of at least two sub-populations each comprising a known active agent capable of specific binding with at least one target analyte, wherein said subpopulations are deposited sequentially and at discrete periods of each other;

making images of said substrate after deposition of each subpopulation; and comparing said images using said fiducial as a reference to thereby determine the location of each microbead and to identify the subpopulation, and its known active agent, based on differences between each image.

Advantageously, decoding of the microbeads is enabled by the comparing step in which the location of each microbead and its respective sub-population relative to said at least one fiducial is determined. More advantageously, because an imaging step is undertaken between successive depositing steps of said microbeads.

Advantageously, the method does not comprise the step of decoding the microarray once all of the microbeads have been placed on the substrate. The decoding is performed during the manufacture of the microarray wile microbeads are being disposed on the substrate.

Advantageously, the microbeads can be deposited on the substrate randomly.

Advantageously, the method does not require the use of an identifier or tag, such as a decoding binding ligand, to determine the location of each microbead and its respective population. Accordingly, in one embodiment, the method does not comprise the step of decoding the microarray using an identifier or tag, such as a decoding binding ligand.

In one embodiment, there is provided a process for making a micro-array comprising:

depositing microbeads of a first sub-population on a substrate having at least one fiducial, said subpopulation comprising a active agent that is capable of specific binding with at least one target analyte;

imaging the microbeads of said first sub-population;

depositing microbeads of a second sub-population on said substrate, said second subpopulation comprising a known active agent that is capable of specific binding with at least one target analyte that is different from said target analyte of said first population;

imaging the microbeads of said first and second sub-populations; and comparing said images of said first and second sub-populations to determine the location of each microbead and its respective sub-population relative to said at least one fiducial.

Accordingly, because the active agent is known for each sub-population, it is not necessary to undertake any further decoding steps to determine the chemical or biological function of the microbeads.

The process may comprise the step of recording data indicating the location of each of said microbeads and its sub-population. The recording step may comprise recording said data in a computer memory.

The active agent may be a bioactive agent. The bioactive agent may be a protein or a nucleic acid.

The process may comprise the step of functionalizing said microbead with a chemically reactive group.

The process may comprise, after deposition of each sub-population, removing said microbeads that have not formed an attachment to said substrate. The process may comprise the step of forming at least one fiducial on said substrate.

The process may comprise the step of forming a three-dimensional structures within said substrate to facilitate containment of said microbeads thereon. The three-dimensional structures may be depressions formed in a substantially flat substrate.

The sequential deposition of said subpopulations for each discrete period may be undertaken from 1 up to 10,000 times.

According to a second aspect of the invention, there is provided a microarray system for identifying the presence of one or more target analytes in a sample comprising:

a random population of microbeads disposed on a substrate surface having at least one fiducial, said population being comprised of at least two sub-populations each comprising a known active agent capable of specific binding with at least one target analyte, wherein said subpopulations had been deposited sequentially and at discrete periods of each other;

a memory recording the location of each microbead and its respective subpopulation relative to said at least one fiducial, said location of each microbead and its respective subpopulation having been determined by comparison of images of said microbeads between said sequential discrete deposition periods;

a detector to detect changes in the said microbeads upon contact with said sample; and a processor responsive to program instructions to interrogate said memory and to compare data received from said detector to identify the presence of said one or more target analytes in said sample based on the location of each microbead and its respective subpopulation.

Advantageously, decoding of the microbeads has been undertaken at the time of manufacturing the system and therefore it is not performed at the time the microarray system is assembled.

The microarray system may comprising decoding data for storage in said memory, said decoding data containing data indicating the location and known active agent of each of said microbeads relative to said fiducial. The decoding data may be in a format for transfer over a computer network, such as the Internet. An identifier may be required to gain access to said decoding data.

According to a third aspect, there is provided a microarray for use in a system for identifying the presence of one or more target analytes in a sample, the microarray comprising a random population of microbeads disposed on a substrate surface having at least one fiducial, said population being comprised of at least two sub-populations each comprising a known active agent capable of specific binding with at least one target analyte, wherein each of said subpopulations have been deposited sequentially and at discrete periods of each other to enable the location of each microbead and its respective sub-population to be determined relative to said fiducial from comparative images taken during each discrete deposition period. According to a fourth aspect, there is provided a process for identifying target analytes in a sample, the process comprising the steps of:

contacting said microarray as defined in the third aspect with said sample;

identifying said microbead subpopulations that have undergone a change that is indicative of said active agent being bound to a target analyte present in said sample; and identifying the presence of any target analyte present in said sample based upon the location and known active agent of said microbeads which exhibit said change.

The change may be an optical change. The process for analyzing said sample may comprise the step of providing an optical signature to indicate binding of said microbead and said target analyte.

DEFINITIONS

The following words and terms used herein shall have the meaning indicated:

The terms "microarray" or "array" as used herein refers to an array of microbeads on a solid support, wherein each microbead has a selected, bioactive agent capable of binding with one or more target analytes. Depending on the size of the microbeads and the substrate, generally, the microarray will comprise from two to as many as a billion or more microbeads.

The term "random array" used herein refers to an array that is manufactured such that each microbead is arbitrarily deposited on the substrate in a generally non-reproducible manner.

The terms "microbead" or "microparticle" and grammatical variations thereof, refer to a micrometer sized discrete microbead in the range of about 0.1 microns to about 1000 microns in diameter.

The term "population" as used herein refers to the total universe of microbeads deposited on the microarray. The terms "subpopulation" as used herein refers to a group of microbeads within the population that all comprise the same active agent.

The term "active agent" may refer to any chemical agent or biological agent that is capable of reacting with the target analyte or an intermediary bound to the target analyte. The active agent may exhibit biological activity and may be referred to in the specification as a "bioactive agent". Exemplary bioactive agents include proteins, oligopeptides, small organic molecules, coordination complexes, cells, cell fragments, virus particles, antigens, polysaccharides and polynucleotides, which can be attached to or bonded to a microbead.

The term "target analyte" refers to a substance to be detected that is capable of binding to said active agent. Exemplary target analytes include, but are not limited to, nucleic acids, polynucleotides, drugs, hormones, proteins, enzymes, antibodies, carbohydrates, and antigens.

The term "specific binding substance" may refer to a substance which has a specific affinity for a certain substance. For example, a target analyte in a sample may be capable of undergoing a specific binding reaction with the active agent. Examples of combinations of the specific substance with the specific binding substance include: antigens with corresponding antibody molecules, a nucleic acid sequence with its complementary sequence, effector molecules with receptor molecules, enzymes with inhibitors, sugar chain-containing compounds with lectins, an antibody molecule with another antibody molecule specific for the former antibody, receptor molecules with corresponding antibody molecules and the like combinations. Other examples of the specific binding substances include a compound which has been chemically modified to such a degree that its specific binding activity still remains intact and a complex body of a compound bound to other components. Examples of combinations of such types of specific binding substances with the specific substances include: a chemically biotin-modified antibody molecule or polynucleotide with avidin, an avidin-bound antibody molecule with biotin and the like combinations.

The term "protein" as used herein may be defined as two or more covalently bonded amino acid, which includes proteins, polypeptides, oligopeptides and peptides.

The terms "amino acid" and "peptide", as used herein refer to both naturally occurring and synthetic amino acid and amino acid chains respectively.

Unless specified otherwise, the terms "comprising" and "comprise", and grammatical variants thereof, are intended to represent "open" or "inclusive" language such that they include recited elements but also permit inclusion of additional, unrecited elements.

As used herein, the term "about", in the context of concentrations of components of the formulations, typically means +/−5% of the stated value, more typically +/−4% of the stated value, more typically +/−3% of the stated value, more typically, +/−2% of the stated value, even more typically +/−1% of the stated value, and even more typically +/−0.5% of the stated value.

Throughout this disclosure, certain embodiments may be disclosed in a range format. It should be understood that the description in range format is merely for convenience and brevity and should not be construed as an inflexible limitation on the scope of the disclosed ranges. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

DETAILED DISCLOSURE OF EMBODIMENTS

Exemplary, non-limiting embodiments of a microarray system, a process for producing microarrays and a procedure for identifying target analytes using said microarrays, will now be disclosed.

There is disclosed in a process for making a microarray. The process comprises the step of depositing a population of microbeads on a substrate having at least one fiducial. The population being comprised of at least two sub-populations, preferably multiple sub-populations, each comprising a known active agent capable of specific binding with at least one target analyte. The subpopulations are deposited sequentially and at discrete periods of each other. The process also comprises the step of making images of the substrate after deposition of each subpopulation. The images are then compared using the fiducial as a reference to thereby determine the location of each microbead and to identify the subpopulation, and its known active agent, based on differences between each image. Hence, the encoding/decoding procedure is carried out during the production process of the microarray and not after its production. This is because sub-populations of known active agents are sequentially deposited during discrete deposition periods and an image is taken of the substrate after deposition of each sub-population. In one embodiment, the position of each microbead relative to the at least one fiducial is recorded. Because images are taken between each deposition step of each sub-population, by comparing the differences between successive images it is possible to know not only the location of each microbead but also the active agent that it contains. Hence, the active agent, chemical or biological, of each microbead on the substrate is known and therefore it is not necessary to perform any decoding of the microarray once the microbeads have been deposited on the substrate.

The process may comprise the step of providing a substrate. The substrate may be selected from the group consisting of silicon, plastic, glass, ceramic, rubber, polymer or a composite thereof. In one embodiment, the substrate is silicon, or silicon dioxide or silicon nitride.

In another embodiment, the substrate comprises a surface that is hydrophobic or hydrophilic. Advantageously, the hydrophobic or hydrophilic surfaces can be utilized to attract sample fluids containing said target analytes and possibly to repeal unwanted fluids. For example, if the target analyte is in an aqueous fluid, the substrate may be hydrophilic to promote attraction of the target analyte to the microbeads.

Exemplary substrates are selected from the group consisting of silicon, modified silicon, glass and modified or functionalized glass, inorganic glasses, plastics, acrylics, polystyrene and copolymers of styrene, polypropylene, polyethylene, polybutylene, polyurethanes, Teflon, polysaccharides, nylon, nitrocellulose, resins, silica, silica-based materials, carbon and metals. Advantageously, in one embodiment, the substrate does not auto-flouresce.

The substrate may contain three dimensional features on its surface. The three dimensional features may be selected from the group consisting of grids, lines, depressions, wells and gel pad structures to facilitate retention of the microbeads on the substrate. In one embodiment, the three dimensional features may serve as fiducials for the spatial position of the microbeads.

The depositing step may comprise the step of forming an attachment between the microbeads and the substrate. The attachment of the microbead onto substrate may be dependent on chemical interactions selected from the group consisting of electrostatic interaction, ionic bonds, covalent bonds, hydrogen bonds, hydrophobic interactions, hydrophilic interactions and dipole-dipole interaction.

Prior to the attaching of the microbead to the substrate, the substrate may be functionalized with chemically reactive groups. Advantageously the chemical fictionalization of the substrate may promote adhesion of the microbeads to the substrate.

Exemplary chemically reactive groups may be selected from the group consisting of thiols, carboxyls aliphatic and aromatic amines, carboxylic acids, aldehydes, amides, chloromethyl groups, hydrazide, hydroxyl groups, sulfonates and sulfates. The sites which are chemically modified through functionalization may be used to attached either covalently or non-covalently to the microbeads. Preferably, the functionalization does not cause any undesirable change in the properties of the substrate.

The step of forming an attachment between the microbeads and the substrate may comprise the step of applying an adhesive material to at least one of the substrate and the microbeads. In one embodiment, the applying of the adhesive material is to the substrate. Exemplary adhesive material that may be used includes acrylic-based, urethane-based, silicone-based and epoxy-based adhesives. Most preferably, the adhesive does not have significant auto-fluorescence.

In one embodiment, the process may comprise the step of applying an adhesive coating to the substrate. In another embodiment, the process may comprise the step of applying an adhesive coating to the microbead before deposition on the substrate.

The process may comprise the step of depositing pre-formed microbeads on the substrate. The process may comprise the step of removing from the substrate surface, those beads which have not adhered to the substrate in said depositing step. The process may comprise the step of imaging the substrate surface after said removing step.

The process may comprise the step of forming a fiducial on the substrate. A plurality of fiducials may be provided on the substrate. Advantageously, the fiducial allows uniform and stable comparison between different images taken between sequential deposition of said microbeads during said discrete periods. Preferably, more than one fiducials are used to reduce inconsistencies when comparing different images.

The fiducials may take a number of forms. In one embodiment, the fiducial may be a bead with a unique optical signature or other detectable characteristic. In another embodiment, fiducials may be in the form of one or more defined edges on the substrate. In yet another embodiment, fiducials may be irregularities found on the surface of the substrate.

The process may comprise the step of recording the position of each attached microbead relative to the fudicial. The recording may be undertaken in the memory of a computer. The position of each microbead relative to the fudicial may be recorded as data in computer memory in the form of data table containing the spatial position of each single microbead and its corresponding subpopulation (hereafter called the "encoding/decoding data table"). Hence the encoding/decoding data table encodes the position of the microbeads and their respective subpopulation on the substrate and can be used as a decode tool to determine the position of the microbeads and their respective subpopulation on the substrate with reference to the fiducial. As described above, each subpopulation has its own unique known active agent on the microbeads and thereby its ability to detect a particular target analyte that may be in a sample.

Advantageously, the position and identifier data associated with each microbead may be recorded in the encoding/decoding data table in the memory of a computer. It can therefore be readily accessed by a processor acting under instructions of a computer program to decode the microarray by determining the position of the microbeads and their functionality relative to the fudicial. The computer readable memory may comprise an acquisition module that may comprise computer code that can receive a data image from a random array and a registration module comprising computer code that can register the data image using at least one fiducial to generate a registered data image. The registered data image may be stored in a storage module as needed. The same computer code, or different code, may be used to receive additional data images and generate additional registered data images, which may also be stored. Preferably, the computer readable memory may further comprise a comparison module comprising computer code that can compare the registered data images to determine the differences between them, to allow both decoding of the array and target analyte detection. The comparison of at least two registered data images allows the identification of the location of at least two unique bioactive agents on the array.

For example, the registered data image between a first subpopulation (data set "RDI-1") and a second sequential subpopulation (data set "RDI-2") are compared. Those new microbeads located in RDI-2 that were not present in RDI-1 are determined to be from the second sequential subpopulation and those that were present in RDI-1 but not RDI-2 are determined to be from the first subpopulation. Likewise, subsequent subpopulation images are compared and assigned to their respective subpopulation groups. The data indicating the position and known active agent of each subpopulations 1, 2, . . . , n are compiled into the encoding/decoding data table.

The encoding/decoding data table for a particular substrate may be provided to the user wanting to analyse a sample potentially containing one or more target analytes. In one embodiment, the user may purchase the microarray with an identifier (ie such as a serial number) located on the microarray. The user may utilize the identifier to access the encoding/decoding data table. For example, by inputting the identifier into a computer program supplied with the miroarray, the identifier may unlock the encoding/decoding data table and make it available for decoding the microarray. Alternatively, the user may input the identifier into a internet-based supplier site which grants access to the encoding/decoding data table (ie by allowing it to be downloaded). This is particularly advantageous as it allows the supplier of the microarrays to control the access to the encoding/decoding data table, which is unique to the microarray.

It is envisaged that because the encoding and decoding of the microarray is performed during the manufacturing steps, the originator of the microarray can have a tighter control over the use of the microarrays and prevent unwarranted copying. This may also be a mechanism by which the originator can be paid for the sale of the microarrays if they receive funds at the time that the encoding/decoding data table is supplied to the end user.

In one embodiment, the disclosed microbeads may be irregularly shaped microbeads or regularly shaped microbeads. The microbeads may also have a shape selected from the group consisting of microspheres, microcapsules, microrods, microcubes and microtubes. Most preferably, said microbeads are microspheres. If a large surface area is desired, the microbeads may also be porous. Exemplary microbeads are formed of material selected from plastics, ceramics, glass, polystyrene, methylstyrene, acrylic polymers, paramagneticmaterials, thoria sol, carbon graphited, titanium dioxide, latex or cross-linked dextrans such as sepharose, cellulose, nylon, cross-linked micelles and teflon or with the similar compositions used in peptide, nucleic acid and organic moiety synthesis.

The microbeads may range in size range from about 100 nm to about 500 µm. More preferably, the microbead sizes range from about 1 µm microns to about 10 µm. Each microbead may be comprised of a plurality of active agents that are attached to, or incorporated within, the microbead structure. In one embodiment, each microbead comprises a single type of bioactive agent.

In one embodiment, the bioactive agents that are attached to said microbeads may be selected from the group consisting of organic and inorganic compounds. Preferably, the bioactive agents are organic compounds. In another embodiment, the bioactive agents are proteins. The protein may be naturally occurring proteins or synthetically synthesized proteins.

The bioactive agents may be naturally occurring proteins or fragments derived from naturally occurring proteins. Cellular extracts containing proteins, or random or directed digests of proteinaceous cellular extracts, may be used as the bioactive agents. In another embodiment, the bioactive agents are nucleic acids. The nucleic acid may be naturally occurring or synthetically synthesized. The nucleic acid may be single stranded or double stranded or contain portions of both double stranded or single stranded sequence. The nucleic acid may be DNA, both genomic and cDNA, RNA or a hybrid.

The naturally occurring biomolecules used as bioactive agents may be in the form of bacterial, fungal, plant and animal extracts or products. The bioactive agents may also be modified through conventional chemical, physical and biochemical means prior to attachment on the microbeads.

The bioactive agents may either be synthesized directly on the microbeads, or they may be made and then attached after synthesis. In one embodiment, linkers are employed to attach the bioactive agents to the microbeads, to provide better attachment, improve interaction with the target molecule due to the increased flexibility, and to reduce undesirable or non-specific binding. The attachment of the bioactive agent onto the microbead may be dependent on chemical interactions selected from the group consisting of electrostatic interaction, ionic bonds, covalent bonds, hydrogen bonds and dipole-dipole interaction. Prior to the attaching of the bioactive agent to the microbead, the microbead may be functionalized with chemically reactive groups to facilitate binding.

In a one embodiment, the target analyte may be organic or inorganic molecules. The target analyte may be selected from the group consisting of a nucleotide sequence a protein, a lipid moiety, a carbohydrate moiety, an enzyme, an antibody and an antigen. In another embodiment, the target analyte is selected from the group consisting of environmental pollutants (including pesticides, insecticides, toxins, etc.); a chemical (including solvents, polymers, organic materials, etc.); therapeutic molecules (including therapeutic and abused drugs, antibiotics, etc.); biomolecules (including hormones, cytokines, proteins, nucleic acids, lipids, carbohydrates, cellular membrane antigens and receptors (neural, hormonal, nutrient, and cell surface receptors) or their ligands, etc); whole cells (including procaryotic (such as pathogenic bacteria) and eukaryotic cells, including mammalian tumor cells); viruses (including retroviruses, herpesviruses, adenoviruses, lentiviruses, etc.); and spores. The target analytes may be nucleic acids and proteins (including immunoglobulins; enzymes hormones and cytokines). The specific binding of the target analyte to the bioactive agent may be dependent on chemical interactions selected from the group consisting of electrostatic interaction, ionic bonds, covalent bonds, hydrogen bonds and dipole-dipole interactions.

When the microarray is being used to analyse a sample potentially containing a target analyte, an optical signature may be added to at least one of the microbeads and the target analyte. Advantageously, the optical signature can be used to enhance the identification of the location of the microbeads and subsequently the bioactive agents on the microbead. The optical signature may exhibit an optical change when the active agent is bound to the target analyte. In one embodiment, the optical signature is applied after the sample containing said target analytes have, bound to the active agents of the microbeads.

The optical signature may be conjugated on the target analyte which in turn binds to the corresponding bioactive agent on the microbead. The optical signature may be directly conjugated to the target analyte or indirectly conjugated to the target analyte by means of a linker molecule.

In a one embodiment, the optical signature may be a mixture of reporter dyes, preferably fluorescent. The variation of the composition of the mixture of reporter dyes may change the output optical signal intensity, providing a large possible range of unique optical signatures.

The process may comprise the step of detecting the optical signatures with a detector, such as an optical detector. The optical detector may send a signal to the computer memory which is then accessed by a computer processor for generating an image file. Data associated with the image file which microbeads exhibit the optical signature, are then compared with the data of the encoding/decoding data table. Those microbeads which exhibit the optical signature are those which have bound with the target analyte. Because the active agent for the subpopulation of the microbeads is known from the encoding/decoding data table, it is possible to identify the target analytes in the sample.

In one embodiment, the process to detect target molecules in a sample by using the encoding/decoding data table and thereby decoding the microarray information comprises the steps of:

i) Incubating a sample containing one or more target analytes with the microarray.

ii) Adding an optical signature in the form of fluorescent or dye or nanogold or quantum dot labeled biomolecules, wherein such biomolecules are oligonucleotides or target molecules or dNTPs or enzyme substrates to facilitate the performance of bioassays and to cause optical signatures at the microbead surface.

iii) Optically reading of the microarray with a detector from the optical signatures to, detect and determine all of the positions of the microbeads with optical signatures at the surface by the use of microscopy or a scanner or a digital or video camera system or by the use of photographic films. The encoding/decoding data table may be retrieved from a computer memory containing the spatial position of all microbeads with their unique active agent for each subpopulation.

iv) Using the data from the encoding/decoding data table and the data table generated from the optical microarray readout to decode and thereby to detect target analytes in a sample by combining and comparing the two data tables and identifying corresponding microbeads in the two datasets and thereby identifying such microbeads and their target analytes in the sample. The decoding process may be automated by using software in a computer and/or wherein parts of the decoding dataset information may be restricted to certain users and/or wherein the decoding dataset or parts of the decoding dataset may be transmitted to the user via the internet or wireless communication means.

In one embodiment, the production process for the microbead based random microarray and its subsequent decoding comprises the steps of:

i) providing a substrate material. The substrate material may consists of multiple chips (e.g. 100 to 10000) or is later diced into multiple chips;

ii) creating a fiducial, such as an identification number, onto the area of each single chip. For example, by using a laser-engraving instrument. Simultaneously, fiducials or reference coordinates that define an x and y position (e.g., 0,0) may be engraved on the substrate;

iii) providing an adhesive layer on the substrate surface;

iv) preparing bulk composition suspensions for each subpopulation of microbeads carrying a particular known bioactive agent for performing a bioassay based on bio-recognition or enzymatic reactions;

v) Treating the substrate with the first subpopulation of microbeads in a way that a sufficient number of microbeads are fixated onto the area of each chip; typically this number is 5 to 20;

vi) Removing loosely anchored microbeads;

vii) Imaging of those anchored microbeads and storage of the corresponding x and y position values for each single microbead and chip with the corresponding chip number in a decoding data table in a memory;

viii) Repeating steps iv) to vi) with the desired number of microbead subpopulations from 2 to n;

ix) Data processing of the image files for subpopulations 1 to n. Thereafter generating a decoding data table for each single chip with x, y position values of each single microbead for each microbead subpopulation from 1 to n; and x) Mounting the chips in a chip holder or device or flow chamber or incubation chamber and packing.

BRIEF DESCRIPTION OF DRAWINGS

The accompanying drawings illustrate a disclosed embodiment and serve to explain the principles of the disclosed embodiment. It is to be understood, however, that the drawings are designed for purposes of illustration only, and not as a definition of the limits of the invention.

FIG. 1 is a schematic illustration of a production process for producing a microarray in accordance with a disclosed embodiment.

FIG. 2 is a schematic illustration of a flow chart for decoding the microarray after application of the sample.

FIG. 3A is an atomic force micrograph of microbeads assembled onto glass substrate in accordance with a disclosed embodiment. The glass substrate was positively charged by its coating with poly (alylamine hydrochlorid). The microbead carries negative charges and is fixated by coulomb forces.

FIG. 3B (i) shows 3-dimensional microbead structures of a first subpopulation are formed on gel pad substrates formed at the surface; (ii) shows 3-dimensional microbead structures of a second subpopulation on the gel pad substrate; and (iii) shows fluorescent images of the first subgroup which is exhibiting fluorescence due to binding with a target analyte;

FIG. 3C shows a Scanning Electron Micrograph of a polystyrol microbead fixated onto a substrate carrying 3-dimensional structures of microwells.

FIG. 4 discloses pictures of a microarray taken at discrete time intervals for two target analytes: FIG. 4A shows the signals from IgG beads, after incubation with Anti-IgG-FITC; FIG. 4B shows the signals from oligo beads after incubation with Cy3-labeled oligo targets; and FIG. 4C shows the signals from the IgG beads, the oligo beads and negative control beads. Two different filters were used to visualize the FITC and Cy3 signals separately as shown in FIGS. 4D and 4E. In FIG. 4D only IgG beads are detected when a filter filtering Cy3 signals are used. In FIG. 4E only oligo beads are detected when a filter filtering FITC signals are used. However, two different dyes are not necessary to perform the analysis.

DETAILED DESCRIPTION

Non-limiting examples of the invention, will be further described in greater detail by reference to specific Examples, which should not be construed as in any way limiting the scope of the invention.

Referring to FIG. 1, there is shown a schematic diagram demonstrating the steps to which the disclosed microarray is produced. There is provided a substrate (1) consisting of sub-substrates (chips m to mx) and at least one fiducial is provided.

In a first step (A), the substrate is treated with the first subpopulation of (n1) (shown for illustration as unfilled circles) and microbeads that are comprised of a first active agent capable of binding to at least one target analyte. Each microbead of subpopulation n1 is comprised of the same bioactive agent on its surface.

In a second step (B) non-fixated microbeads are separated or washed off the substrate.

In a third step (C), the attached microbeads are imaged and their x,y coordinate positions relative to at least one fiducial are stored in a data set related to the batch number (e.g. n1) and the chip number (e.g. m26), in the form of a encoding/decoding data table.

In the following steps (D) to (x) the procedure described in step (A) to (C) is repeated sequentially with subpopulation n2 to nx until the desired number of microbead subpopulations has been applied onto the substrate. At the end of the process, a substrate carrying "nx" batches and a encoding/decoding data table containing all x,y particle positions for each batch will result.

Referring to FIG. 2, there is shown a schematic diagram of the steps to which the disclosed microarray is decoded and how the analytes in a sample are identified. The decoding process is carried out in a series of steps.

In the first step (A), a microarray fabricated by the disclosed in one embodiment and its unique decoding data table created during the fabrication process are provided.

In a second step (B), a sample containing potential target analytes is incubated with the microarray. Any binding of the target analytes in the sample to the corresponding active agents on the microbeads are based on (i) hybridization and elongation by polymerase and/or (ii) antibody antigen interaction and/or (iii) enzymatic reactions. Upon binding and interaction of the target analytes with active agents on the microbeads, optical signatures are produced. The microarray is then washed to remove any unspecific binding with the microbeads and consequently remove any undesired optical signatures that are present on the microarray.

In the next step (C), a video or CCD camera is used to detect the x, y co-ordinate positions (relative to at least one fiducial) of the microbeads that are carrying a optical signature on their surface and the readout data is input into a computer to generate a readout data table.

In the next step (D), the decoding/encoding data table is combined and compared with the readout data table thereby decoding the microarray to identify the target analytes that are present in the sample.

I) Calculation of Data File Size Per Chip

Hereafter, the word "chip" will mean a portion of an array or microarray that has been diced.

The data set of each chip consists of n subsets, wherein n is the number of microbead subpopulations used to create the chip. Each data subset determines the x,y positions for all microbeads originated from the subpopulation. The data set enables the encoding of each microbead due to its x and y position relative to a fiducial in the form of a marker structure on the chip.

For example: The is the chip is square shaped having the dimensions of 2 mm×2 mm and the microbead diameter is 5 µm, the average microbead distance is 5 µm, which is calculated as follows:

The average number of microbeads per 2mm=2000mm/(5 µm+5 µm)=200.

Therefore, the average microbead number per chip is:

200×200=40000.

The average number of microbeads per subpopulation (sub-pn), with a number of n subpopulations is:

sub-$pn$=40000/$n$.

High-resolution video cameras provide a resolution of 2048 pixel×2048 pixels. The optical resolution of a visible field of 2 mm×2 mm is about 1 µm. A computer scanner has a typical resolution of 4800×4800 dpi (dots per inch). The optical resolution is about 5.3 µm. This resolution is sufficient to determine microbead positions of microbeads with a diameter larger then 6 µm. By using a computer scanner, microbeads should suitably have diameters of 100 to 500 µm.

The pixel number 2048 is equivalent to $2^{12}$. To store numbers up to 2048, 12 bits are required. Each microbead position can be determined by a 12 bit number for its x and y value. One microbead requires 24 bits or 3 byte. Hence, to store the positions of all 40000 microbeads, 120000 bytes or 117 kilobyte are required. This data volume can be stored on any data media or is accessible over the Internet in seconds.

The data volume increases with the number of microbeads and with decreasing size of the microbead. For example, a 2 mm×2 mm chip with 1 µm microbeads and 1 µm average microbead distance can hold $10^6$ microbeads. Each microbead requires about 6 bytes. Total about 7.6 Mbytes.

II) Preparation of Bead Based Arrays

Multi Chip Production

A substrate with a size of for example 20 cm×20 cm is treated with a suspension of microbead particles by simply applying the suspension onto the surface of the substrate or by airbrushing with a microbead suspension in the sequential process described above, thereby forming a microarray.

After all subpopulations of microbeads are applied and the encoding/decoding data table is generated, the substrate is diced into single chips of 2 mm×2 mm to generate a total number of up to 10000 chips in parallel. Each single chip should carry an identifier to match the correct data from the decoding data table with the chip.

Mounting of the Bead Based Array

The array can be mounted into a holder, a flow through device, a lateral flow device, a transversal flow device. In any case the array is subjected to come into contact with the sample and reagents. Reagents are provided by releasing them from a release pad in, for example, a lateral or transferal flow device, or by depositing them onto the surface of the array or by mixing them with the sample prior to its application onto the array. A transparent window is mounted above the array at a distance of 10 to 500 µm forming a cavity which can be filled with the analyte/reagent mixture. The cavity may be a part of a flow channel.

Sample Application Procedure

Reagents are mixed with the sample prior to its application or in the device. In a typical lateral flow based device the sample is added and transported through the device by capillary forces. Reagents are typically released from release pads through which the sample must travel to reach the microarray. To provide a continuous transport of the sample over the microarray, a sucking pad may be placed behind the microarray. Removal of the sample and reagents from the array are achieved by capillary force based transport and/or washing with a buffer or water and/or centrifugation forces.

Read Out Procedure

After incubation with the sample and separation of non reacted components the array can be read out by fluorescent measurements, reflection photometry, and transmission photometry luminescent measurements. A state of the art scanner or optical drive operable by a personal computer is used as an optical detector. Read out data is able to be altered or corrected by using calibrations or software programs specifically adapted to the scanner being used. During the read out, the following data will be obtained:

(i) an image containing the intensity or signals for all microbeads;

(ii) an image containing the position of fiducials in the form of marks relative to all microbeads;

(iii) an image containing information correlated to the production of the array in particular the subpopulation number, production date, array number and/or any other information or encoded information necessary to perform analysis with the array.

From the images containing the above information the following data can be generated:

i) intensity/signal for all beads at a defined x, y position relative to marks; and ii) any other data necessary to perform analysis with the array, in particular data to correlate the correct encoding data set to the array.

EXAMPLES

Example 1

This example illustrates application of the microbead-based microarray for detecting single-nucleotide polymorphisms (SNPs).

An array of polyacrylamide gel pads were fabricated onto the surface of a glass slide using ultra-violet photopolymerization. Each discrete gel pad was further comprised of a square array of micropillars. Four sets of beads were prepared by separately conjugating them with oligonucleotide probes for targeting a particular SNP. These four probes contained all the possible single nucleotide permutations of ATGC at the target SNP site. The first set of conjugated beads was fixated onto a specified gel pad using micro-targeting with a robotic dispenser. Loosely anchored beads were washed away before the remaining fixated beads were imaged using a CCD camera system. Positions of all the fixated beads were decoded from this image, and the data stored in a computer memory. This process was then repeated sequentially for a second set of conjugated beads over the same gel pads.

An optimized hybridization buffer containing oligonucleotides of the target SNPs was then applied over the fixated beads. Positive hybridization signals from the beads were then detected using a CCD imaging system. These signals were identified since the beads had already been decoded based on their positions. This allowed the target SNPs to be easily detected. Multiplexed detection of many SNP can be achieved by repeating this method to fixate four sets of beads over each gel pad for a high-throughput genotyping platform. Four other sets of beads for targeting a second SNP site were fixated in the same manner onto another gel pad but these are not shown in the figures.

Example 2

This example illustrates application of the microbead-based microarray for detecting fecal indicator bacteria in environmental samples.

Twenty sets of probes were designed to target 16S rRNA regions of ten fecal indicators. Each fecal indicator was targeted by a pair of perfect match (PM) and mismatched (MM) probes that differ by a single nucleotide at the middle portion. Using the same method described in Example 1, the ten sets of beads conjugated with PM probes were fixated onto different gel pads, and the positions of beads within each gel pad characterized. This was repeated for the beads conjugated with MM probes, such that each gel pad contained beads conjugated with the pair of probes for targeting a particular fecal indicator. These two sets of beads were distinguished based on their spatial codes.

Environmental samples suspected of containing the fecal indicators were prepared and hybridized to the fixated beads. Based on the relative hybridization signals between the PM and MM probes for each of the ten gel pads, the presence of fecal indicators in the unknown environmental samples was detected. This system can easily be expanded to detect more than ten fecal indicators by fixating further sets of beads onto other gel pads.

Example 3

This example demonstrates the performance of antibody based assays using antibody antigen interaction and DNA based assays using DNA/DNA or DNA/RNA hybridization on the same chip in parallel.

Preparation of Antibodies by Biotinylation:

Antibodies (polyclonal Mouse IgG and polyclonal Mouse Anti-IgG) were diluted to approximately 2 mg/ml. Biotin-NHS (10 mg/ml, dissolved in DMSO) was added to the antibody solution at the molar ratio (Mbiotin:MAntibody) of 1:1, 5:1 and 10:1. The reaction tube was incubated at 25° C. overnight. The biotinylated antibody was purified using a gel-filtration column (D-Salt dextran desalting column, Pierce). The biotinylated antibody was dissolved in the PBS and stored at −20° C.

Protocol for FITC Conjugation of Antibody:

Antibodies (polyclonal Mouse IgG and polyclonal Mouse Anti-IgG, Arista Biological inc.) were diluted to approximately 2 mg/ml. FITC was added (10 mg/ml, dissolved in DMSO) to the antibody solution at the molar ratio (Mbiotin: MAntibody) of 5:1, 10:1 and 20:1. The reaction was incubated in a tube at 25° C., overnight. The FITC-antibody was purified using a gel-filtration column (D-Salt dextran desalting column, from Pierce Biotechnology Inc.). The FITC-antibody was dissolved in PBS and stored at −20° C.

Preparing Antibody Coated Microbeads (Subpopulation 1):

Streptavidin-coated polystyrene beads 9.95 μm in diameter (Bangs Laboratories, Fishers, Ind.) were used for the immobilization of antibodies. Biotinylated antibodies were added to the beads suspension in the amount of 0.5 micrograms per 1 microliter of original microbeads (excess 2.5 times). Incubatation was undertaken at 25° C., overnight. The unbound antibodies were washed out with PBST-B (1×PBS, 0.05% Tween-20, 1% Bovine Serum Albumin) for 2-3 times before use. These beads are then be placed on a substrate as shown in FIG. 4A.

Preparation of Oligonucleotide Functionalized Microbeads (Subpopulation 2):

Streptavidin-coated polystyrene beads 9.95 μm in diameter (Bangs Laboratories, Fishers, Ind.) were used for the immobilization of the oligonucleotide. 100 μL of stock beads (1% solids) was rinsed three times in TTL buffer (100 mM Tris-HCl, pH 8.0, 0.1% Tween 20, 1 M NaCl), precipitated and then resuspended in 20 μL TTL. Following that, 0.5 μL of stock probes (0.5 μg/μl) was added in excess to the binding capacity of the microbeads, which was found to be ~330 ng DNA per mg of microbeads. Capture probes (5'-GCCCT-CACGATCTCTTCC-3') biotinylated at the 5' end were immobilized onto the microbeads via the biotin-streptavidin binding by gently mixing at room temperature for 12 h. After immobilization, the microbeads were rinsed, precipitated, and resuspended in TTE buffer (100 mM Tris-HCl, pH 8.0, 0.1% Tween 20, 20 mM EDTA) at 80° C. for 10 min to remove unstable biotin-streptavidin bonds. These beads are then be added to a microarray comprising antibody coated microbeads as shown in FIG. 4B.

Fabrication of Bead-Based Array:

Deposition of bead subpopulations of antibody coated beads (Subpopulation 1) (FIG. 4A) and oligonucleotide coated beads (Subpopulation 2) (FIG. 4B) onto the microarray substrate was performed as described above. A third subpopulation of microbeads which are negative control and does not comprise any active agent, may be deposited onto the substrate (FIG. 4C). The device consisted of an array of 19×24 polyacrylamide gel pads fabricated on a glass slide (Corning, Corning, N.Y.) pre-treated with Bind Silane (GE Healthcare, Piscataway, N.J.). The gel pads had a horizontal and vertical pitch of 300 μm, and each gel pad further comprised a 10×10 array of micropillars (10×10×10 μm) with horizontal and vertical pitch of 10 μm.

A photopolymerization process was used to create the array of gel pads. A photomask was affixed onto a silanized glass slide coated with acrylamide solution, and exposed to UV irradiation in a cross-linker (UVC500, Hoefer, San Francisco, Calif.) for 45 min. Areas of the acrylamide solution that were exposed to UV light and underwent polymerization, resulting in the formation of the gel pads on the glass surface. The 10-mm height of the gel pads was determined by Teflon spacers firmly sandwiched between the photomask and the glass slide. After polymerization, the glass slide was treated in 0.1M $NaBH_4$ for 30 min to reduce auto-fluorescence of the gel pads. The Biochip Arrayer (PerkinElmer, Boston, Mass.) was used to deliver 5 nL of different bead types (~9000 beads/μL) onto the gel pads. Alternatively, the beads can also be manually spotted using a pipette, although this is less precise and the beads cover several gel pads simultaneously.

The positions of each spotted single bead was recorded via phase contrast images for determining their spatial addresses. This was then repeated until all bead subpopulations for detecting a particular target were immobilized on the same gel pad. The device was then capped with a microfluidic module for sample flow-through. Alternatively, the buffer can also be applied over the spotted beads without the module. The polydimethylsiloxane (PDMS) module was fabricated using common soft lithographic techniques.

Simultaneous DNA and Immunoassay:

A sample containing antigen and complementary DNA was incubated with the array. The sample contained 0.1 ng/μL of Cy3-labeled DNA target (5'-AGGAAGAGATCGT-GAGGGCA-3') and FITC-labeled anti-IgG, 500 mM NaCl and PBS-T buffer. 10 μL sample was spotted onto the bead microarray. After 30 min incubation, the array was rinse briefly with 20 μL of a solution containing 500 mM NaCl and PBS-T, and the signals were then registered by fluorescence microscopy. FITC-labeled anti-IgG that are bounded to the microbeads are illustrated by the illuminated fluorescent circles in FIG. 4D. Cy3 labeled DNA that are bounded to the microbeads are illustrated by the illuminated fluorescent circles in FIG. 4E. It should be noted that the process of identifying target analytes in a sample does not require multiple optical signatures to be used since the exact locations of each microbead is already known. The use of FITC and Cy3 labels are purely for illustrative purposes in this example.

Example 4

A first subpopulation of microbeads comprising of a known first bioactive agent are added to a substrate, subsequently washed and a data image is captured (FIG. 3Bi) and stored in a form of an encoding/decoding data table. A second subpopulation of microbeads comprising of a known second bioactive agent are then added to a substrate, subsequently washed and a data image is captured (FIG. 3Bii) and stored in a form of an encoding/decoding data table. The two encoding/decoding data tables are then combined to form a consolidated encoding/decoding data table as shown in Table 1 below. The location of each of the microbeads with respect to a fiducial (X=0, Y=0 as shown in FIG. 3B) can be determined by comparisons of the data from the consolidated encoding/decoding data table as shown in Table 1 below. A sample containing potential target analytes conjugated with fluorescent dyes are added to the microarray of microbeads. The microarray is washed and viewed under fluorescent microscopy (FIG. 3Bii) and the image is recorded and compared with the consolidated table encoding/decoding data table as shown in Table 1 below to identify the target analyte that is present in the sample.

A decoding data set is generated containing the x, y position values of each microbead; an example data set for FIG. 3B is given in Table 1 below.

In FIG. 3B(i), each of the beads from the first batch are provided on the substrate. In FIG. 3B(ii), each of the beads from the second batch are shown in the figure with an "x". Hence, the computer program reviews images shown in FIG. 3B(i) and FIG. 3B(ii) and determines that the additional beads belong to the second sub-population. The large "X" shown in the top left hand corner is the fiducial.

TABLE 1

Decoding data table of microbeads shown in FIG. 3 B. The microbeads derived from a particular subpopulation, coated with biorecognition molecules/bioactive agents. As shown in FIG. 3B(iii), the 1$^{st}$ batch is shown as being illuminated with a fluorescent dye. It should be appreciated that the FIGS. 3B(i)-(iii) only show two batches (sub-populations of microbeads) on the substrate for illustration. In practice, it is possible to runs 100 s of sub-populations on a substrate and thereby be able to identify a greater number of target analytes.

Array Identification number: e.g. array116
Subpopulation identification table

| Subpopulation No. | Biactive agent coating |
|---|---|
| 1 | Species 1 |
| nx | Species x |

Microbead position data sets

| Subpopulation No: 1 | | Subpopulation No: 2* | |
|---|---|---|---|
| x-position | y-position | x-position | y-position |
| 88 | 22 | 88 | 22 |
|  |  | 212 | 22 |
|  |  | 242 | 22 |
| 26 | 51 | 26 | 51 |
| 57 | 52 | 57 | 52 |
|  |  | 88 | 52 |
|  |  | 119 | 40 |
| 118 | 48 | 118 | 48 |
|  |  | 119 | 56 |
|  |  | 149 | 52 |
|  |  | 212 | 53 |
| 273 | 53 | 273 | 53 |
| 26 | 82 | 26 | 82 |
| 119 | 83 | 119 | 83 |
| 150 | 83 | 150 | 83 |
| 180 | 83 | 180 | 83 |
|  |  | 191 | 83 |
| 212 | 84 | 212 | 84 |
| 272 | 84 | 272 | 84 |
| 26 | 114 | 26 | 114 |
|  |  | 83 | 113 |
|  |  | 89 | 104 |
| 212 | 115 | 212 | 115 |
|  |  | 243 | 115 |
| 273 | 115 | 273 | 115 |
| 119 | 134 | 119 | 134 |
| 118 | 145 | 118 | 145 |
| 150 | 145 | 150 | 145 |
| 242 | 147 | 242 | 147 |
| 56 | 176 | 56 | 176 |
| 88 | 176 | 88 | 176 |
|  |  | 98 | 175 |
|  |  | 180 | 176 |
| 211 | 177 | 211 | 177 |
| 88 | 207 | 88 | 207 |
| 118 | 207 | 118 | 207 |
|  |  | 118 | 207 |
|  |  | 118 | 218 |
|  |  | 149 | 201 |
|  |  | 148 | 212 |

TABLE 1-continued

Decoding data table of microbeads shown in FIG. 3 B. The microbeads derived from a particular subpopulation, coated with biorecognition molecules/bioactive agents. As shown in FIG. 3B(iii), the 1$^{st}$ batch is shown as being illuminated with a fluorescent dye. It should be appreciated that the FIGS. 3B(i)-(iii) only show two batches (sub-populations of microbeads) on the substrate for illustration. In practice, it is possible to runs 100 s of sub-populations on a substrate and thereby be able to identify a greater number of target analytes.

| 179 | 208 | 179 | 208 |
|---|---|---|---|
| 241 | 208 | 241 | 208 |
| 271 | 207 | 271 | 207 |
| 25 | 238 | 25 | 238 |
| 87 | 238 | 87 | 238 |
| 180 | 239 | 180 | 239 |
| 236 | 238 | 236 | 238 |
| 247 | 238 | 247 | 238 |
| 272 | 227 | 272 | 227 |
|  |  | 272 | 237 |
| 27 | 268 | 27 | 268 |
| 118 | 268 | 118 | 268 |
| 178 | 268 | 178 | 268 |
| 272 | 269 | 272 | 269 |
|  |  | 86 | 287 |

*Data read out from the second image contains x, y positions of microbeads from both subpopulations 1 and 2. This data can be used to verify effective fixation of microbeads from subpopulation 1 as shown in FIG. 3B(ii).

APPLICATIONS

It will be appreciated that the process for making a microarray disclosed herein is a cost efficient production process and requires only the use of simple readout equipment.

Advantageously in the disclosed process, the microbead microarray is decoded during its production process. This is in contrast to known state-of-the-art microbead microarray technologies, where the array is decoded after it is generated.

More advantageously, since the encoding/decoding step is implemented into the production process and decoding data is provided with the array, analysis is performed much faster with no decoding procedure needed.

Advantageously, the disclosed microbead microarray can be used with much simpler readout instrument without the requirement of multi wavelength measurements.

Advantageously, the disclosed microbead based microarrays allows: i) to restrict access to analytical data for the user of the array, but analytical data can be generated at any later time after the decoding dataset for a particular analyte is disclosed to the user, and ii) allow access to analytical data for a user by sending encoding data sets via email, Internet, mobile phone, mail or other means of data transfer.

More advantageously, the control to the access analytical data by providing encoding data, allows for more secure data exchange in governments, companies or health care organizations. For example, a measurement is carried out at place "A", but no analytical data can be generated at place "A". Measurement data is transferred to place "B" and is combined with the decoding datasets to generate analytical data. In another example, measurements are carried out with a sample provided by person "P1". No analytical data can be generated from the measurement unless person "P1" or another person "P2" provides the dataset for whichever reason.

Advantageously, the control to the access analytical data may offer potential commercial possibilities. For example, the microarray readout may contain all the analytical data for all the target analytes, but the user is only give access (decoding data) to the particular analyte he/she has paid for.

Advantageously, since analysis is performed much faster with no decoding procedure needed, detection of diseases such as nonpotyposis colon cancer, breast cancer Alzheimer's disease, cystic fibrosis, tuberculosis, Chlamydia and HIV may be expedited. More advantageously, the disclosed microarray may also improve the speed of forensic "DNA fingerprinting" matching.

While reasonable efforts have been employed to describe equivalent embodiments of the present invention, it will be apparent to the person skilled in the art after reading the foregoing disclosure, that various other modifications and adaptations of the invention may be made therein without departing from the spirit and scope of the invention and it is intended that all such modifications and adaptations come within the scope of the appended claims.

3. The micro-array system as claimed in claim 1, wherein said microbeads are in the preferred size range from 100 nm to 500 μm.

4. The micro-array system as claimed in claim 1, wherein the microbeads are attached to the substrate.

5. The micro-array system as claimed in claim 1, wherein the substrate comprises a three-dimensional structure to facilitate attachment of said microbeads thereon.

6. The micro-array system as claimed in claim 5, wherein said three-dimensional structure comprises depressions formed in a substantially flat substrate.

7. The micro-array system as claimed in claim 1, wherein an adhesive coating is present on the substrate or is applied to the microbeads to facilitate attachment of the microbeads thereon.

The invention claimed is:

1. A micro-array system for identifying the presence of one or more target analytes in a sample comprising:
   a population of microbeads which have been randomly deposited on a substrate surface to form a micro-array, said population being comprised of at least two sub-populations each comprising a same active agent capable of specifically binding with a target analyte, the same active agent of each sub-population being different from the same active agent of each other sub-population; and
   a decoding data set table comprising information about the spatial location of each microbead and the sub-population each microbead belongs to;
   wherein the microbeads do not comprise an identifier or tag for determining the location of each microbead and the respective sub-population to which each of the microbeads belongs.

2. The micro-array system as claimed in claim 1, wherein said active agent is a bioactive agent, and may optionally be at least one selected from the group consisting of a protein, a nucleic acid, an enzyme, a cell, a virus particle, an antibody and an organic or inorganic compound.

8. The micro-array system as claimed in claim 1, wherein the decoding data set table or parts thereof are capable of being transmitted to the user via internet or wireless communication means.

9. The micro-array system as claimed in claim 1, wherein the target analyte is at least one selected from the group consisting of a nucleic acid, a polynucleotide, a drug, a hormone, a protein, an enzyme, an antibody, a carbohydrate, an antigen, a lipid, an environmental pollutant, a chemical, a therapeutic molecule, a biomolecule, a whole cell, a virus, and a spore.

10. A process for identifying target analytes in a sample, the process comprising the steps of:
   contacting a micro-array as defined in claim 1 with said sample;
   identifying microbead sub-populations that have undergone a change that is indicative of said active agent being bound to a target analyte present in said sample; and
   identifying the presence of any target analyte present in said sample based upon the location and known active agent of said microbeads which exhibit said change using a decoding data set table as defined in claim 1.

11. The process as claimed in claim 10, wherein said change is an optical change.

12. The process as claimed in claim 10, comprising the step of providing an optical signature to indicate binding of said microbead and said target analyte.

\* \* \* \* \*